United States Patent
Heinold et al.

(10) Patent No.: US 6,768,916 B2
(45) Date of Patent: Jul. 27, 2004

(54) PATIENT-SUPPORTING APPARATUS FOR A PIECE OF MEDICAL EQUIPMENT

(75) Inventors: Michael Heinold, Speichersdorf (DE); Wilhelm Strasser, Obermeitingen (DE); Matthias Seufert, Oberreichenbach (DE)

(73) Assignee: Siemens AG, Munich (DE)

( * ) Notice: Subject to any disclaimer, the term of this patent is extended or adjusted under 35 U.S.C. 154(b) by 229 days.

(21) Appl. No.: 10/026,693

(22) Filed: Dec. 27, 2001

(65) Prior Publication Data

US 2002/0129446 A1 Sep. 19, 2002

(30) Foreign Application Priority Data

Dec. 27, 2000 (DE) .......................................... 100 65 399

(51) Int. Cl.⁷ ................................................ A61B 5/05
(52) U.S. Cl. ............................. 600/415; 5/601; 5/943; 600/407
(58) Field of Search ................................. 600/415, 411, 600/427, 407; 5/601, 630, 943

(56) References Cited

U.S. PATENT DOCUMENTS

| | | | | |
|---|---|---|---|---|
| 4,310,935 A | * | 1/1982 | Stevens et al. ................. | 5/601 |
| 4,761,000 A | * | 8/1988 | Fisher et al. .................... | 5/608 |
| 5,762,073 A | * | 6/1998 | Choy ........................... | 128/846 |
| 6,421,854 B1 | * | 7/2002 | Heimbrock ..................... | 5/610 |
| 2002/0095722 A1 | * | 7/2002 | Korver et al. ............. | 5/81.1 R |

FOREIGN PATENT DOCUMENTS

| | | |
|---|---|---|
| DE | 183210 | 3/1906 |
| DE | 73 29 378.4 | 2/1975 |
| DE | 42 24 036 C1 | 5/1993 |

* cited by examiner

*Primary Examiner*—Eleni Mantis Mercader
(74) *Attorney, Agent, or Firm*—Young & Thompson

(57) ABSTRACT

A patient-supporting apparatus (1) for a piece of medical equipment (15), in particular for an MRI tomograph, has a panel (5) for supporting a patient (3) or for bearing a separate supporting panel. Also provided is a guide element (7) on which the panel (5) is arranged in a displaceable manner such that it can be introduced into an accommodating region (13) of the piece of medical equipment (15). The patient-supporting apparatus (1) is distinguished in that a handle (21) provided for displacing the panel (5) is of pivotable configuration. Preferably integrated in the handle (21) is an actuating element (31) which can bring about an operation for braking the panel (5) in relation to the guide element (7).

18 Claims, 3 Drawing Sheets

PATIENT-SUPPORTING APPARATUS FOR A PIECE OF MEDICAL EQUIPMENT

DESCRIPTION

Patient-supporting apparatus for a piece of medical equipment

The invention relates to a patient-supporting apparatus for a piece of medical equipment, in particular for an MRI tomograph, having a panel for supporting a patient or for bearing a separate supporting panel, and having a guide element on which the panel is arranged in a displaceable manner, it being possible for the panel to be introduced preferably into an accommodating region of the piece of medical equipment.

BACKGROUND OF THE INVENTION

Such a patient-supporting apparatus is used, for example, in the case of an MRI tomograph or in the case of a computer tomograph, which for this purpose are set up in an examination room. The respective piece of medical examination equipment has an accommodating region in which the patient, or part of the patient, is scanned for imaging purposes. A panel, on which the patient can lie down, is provided in the accommodating region. In order to scan a relatively large area of the patient, it is possible for the patient, lying down on the panel, to be guided through the accommodating region.

The patient is usually brought into the examination room lying on a trolley with a supporting panel. According to a first variant, the piece of medical equipment does not have a fixed patient-supporting apparatus. Rather, the trolley serves as a patient-supporting apparatus and the supporting panel of the trolley serves as the abovementioned panel. The trolley has a guide element by means of which the panel or supporting panel, together with the patient, can be guided into the accommodating region and/or through the same. According to a second variant, the piece of medical equipment has a fixed patient-supporting apparatus which can be fixedly connected to a housing of the piece of equipment. The patient, in the examination room, is then laid on the panel of the patient-supporting apparatus either directly or lying on the supporting panel of the trolley. The patient is thus either transferred or laid on the panel of the patient-supporting apparatus together with the supporting panel removed from the trolley. The panel is mounted on a table framework of the fixed patient-supporting apparatus, for example, such that it can be displaced by means of a guide element. This makes it possible, with the patient lying down, for that area of the patient which is to be scanned to be moved into the accommodating region of the piece of medical equipment and moved out again following the examination.

In the case of the known patient-supporting apparatuses, the work which is necessary for positioning the patient in the accommodating region is frequently obstructed. In particular, the abovementioned work required for transferring the patient or for transporting the supporting panel is usually very laborious for the hospital staff.

SUMMARY OF THE INVENTION

The object of the invention is to specify a patient-supporting apparatus with the aid of which a patient can be conveyed to the piece of medical equipment in a more ergonomic manner and with less physical exertion being required.

This object is achieved according to the invention in that a handle provided for displacing the panel is of pivotable configuration, it being possible for the handle to be pivoted from a first position, which is on the patient side and in which the handle projects upward beyond the panel, into a second position, in which the handle is directed away from the patient and is located beneath the panel.

The patient-supporting apparatus according to the invention either is a fixed patient-supporting apparatus of the type described in the introduction or is configured as a trolley—as has likewise been described in the introduction.

The handle can easily introduce a force which is necessary for displacing the panel, it being possible, by virtue of the pivotability of the handle, for the latter to be pivoted away if it is disruptive, for example, during transfer of the patient. According to a preferred embodiment, the handle can be pivoted through a pivoting angle of at least 150°.

In the case of the patient being displaced while lying down, the first position is, in particular, a position in which the handle projects upward beyond the panel and in this case is located, to the greatest extent, vertically. In the second position, it is possible for the handle to be pivoted, for example, beneath the panel and in this case likewise to be oriented vertically downward.

The handle can preferably be pivoted about an axis parallel to the panel.

According to a particularly preferred embodiment, integrated in the handle is an actuating element which can bring about an operation for braking, in particular securing, the panel in relation to the guide element. This easily makes it possible for the staff to release the panel from the arrested state and to brake the panel, displaced by a pushing action, with the patient, if the patient is positioned correctly in the accommodating region, quickly and without any significant physical exertion being required.

According to another preferred embodiment, a braking device is fitted on the panel, the actuating element being configured such that the braking device can be actuated thereby if the handle is located in the first position. In the second position, it is possible for the actuating element to be pivoted together with the handle such that action on the braking device is not possible.

For this purpose, the braking device is preferably configured such that it achieves a braking action if it is not subjected to any action. Provided for this purpose, for example, is a spring element which presses a braking jaw against the guide element or the table framework. If the handle is in the first position, it is then possible, by virtue of the actuating element being actuated, to act on the braking device and thus to release or to reduce the braking force.

The actuating element is preferably designed as a lever which can be pivoted with the handle and, in the first position thereof, engages in a contact element of the braking device in the panel.

The handle is preferably designed as a grip which can be grasped by the human hand and, in particular, is adapted to the shape of the human hand.

BRIEF DESCRIPTION OF THE DRAWINGS

An exemplary embodiment of a patient-supporting apparatus according to the invention is explained in more detail hereinbelow with reference to FIGS. 1 to 3, in which.

DESCRIPTION OF THE PREFERRED EMBODIMENTS

Figure 1:
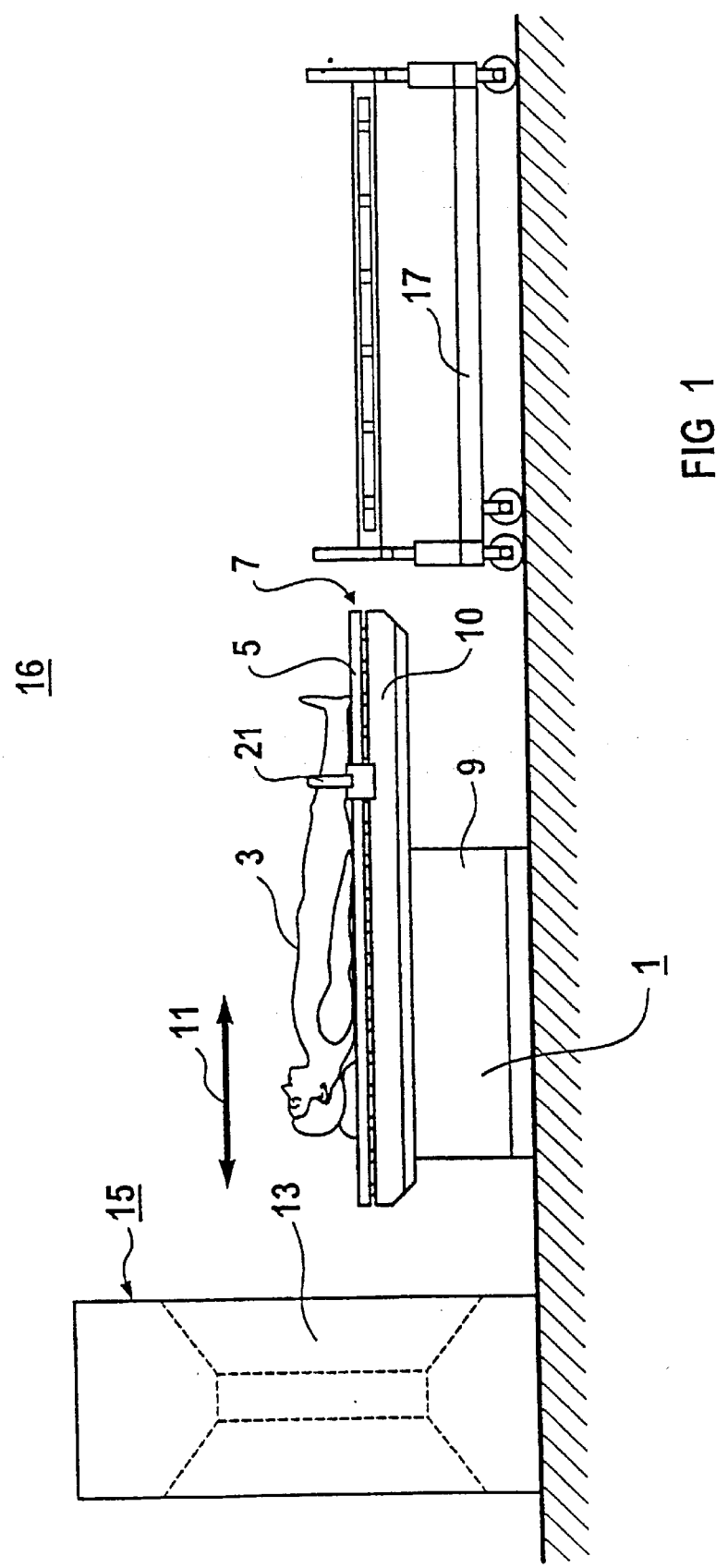
FIG. 1 shows a schematic overview of a piece of medical equipment together with a patient-supporting apparatus.

FIG. 1 shows a side view of a patient-supporting apparatus 1 on which a patient 3 is supported on a panel 5. It is alternatively possible for the panel 5 to be designed for accommodating a supporting panel which, for its part, accommodates the patient 3.

The panel 5 is arranged on the top framework part 10 of a bed base or table framework 9 by means of a guide element 7, for example a guide rail.

The panel 5 with the patient 3 can be moved, along a displacement direction 11, into an accommodating region 13 of a piece of medical equipment 15 and moved out of the latter again following the examination. The piece of medical equipment 15 is, for example, an MRI tomograph, a computer tomograph or some other large piece of medical equipment.

The piece of medical equipment 15 and the associated patient-supporting apparatus 1 are arranged in an examination room 16, into which the patient 3 has been brought by means of a trolley 17. The trolley 17 has been moved laterally alongside the panel 5 and the patient 3 has then been lifted onto the panel 5 by the hospital staff.

In order to displace the panel 5 in the displacement direction 11, i.e. in order to introduce a force which brings about or aids movement, said panel has one or more lateral handles 21.

Figure 2:
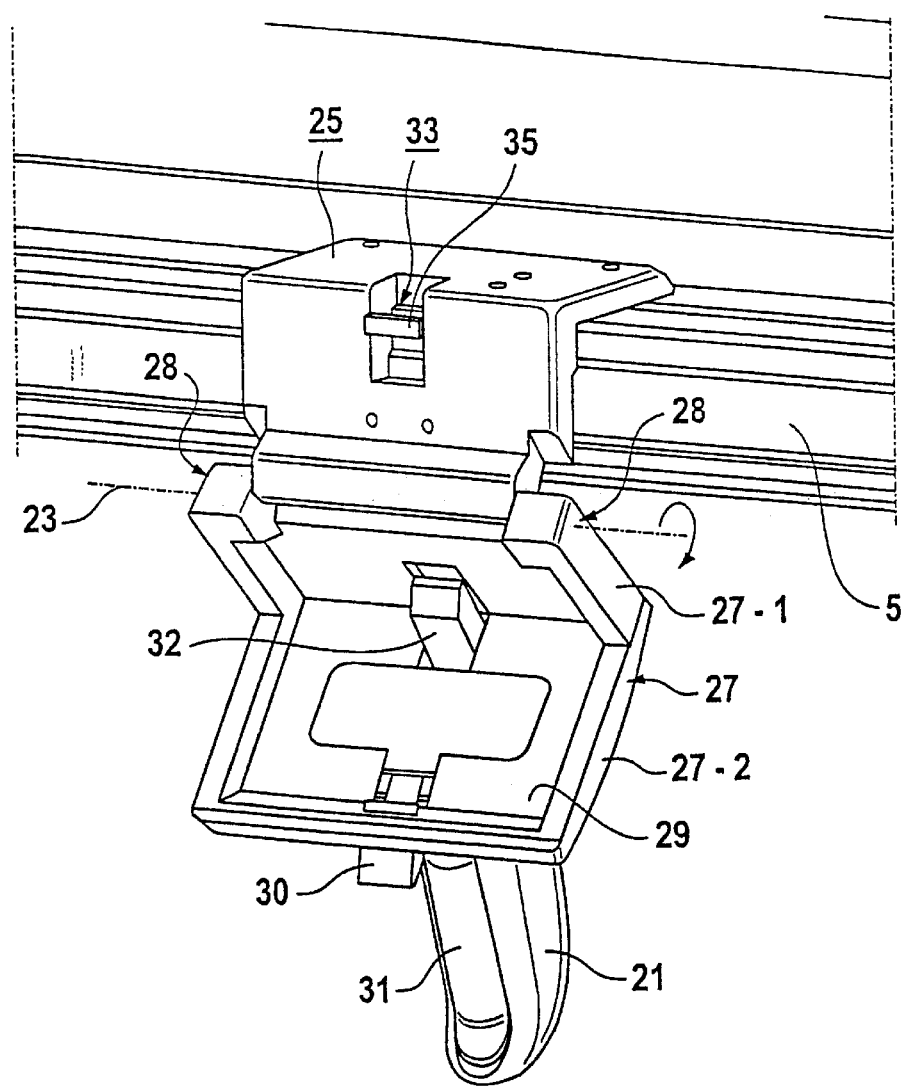
FIG. 2 shows a detail of the patient-supporting apparatus from FIG. 1 with a pivotable handle in a bottom position.
Figure 3:
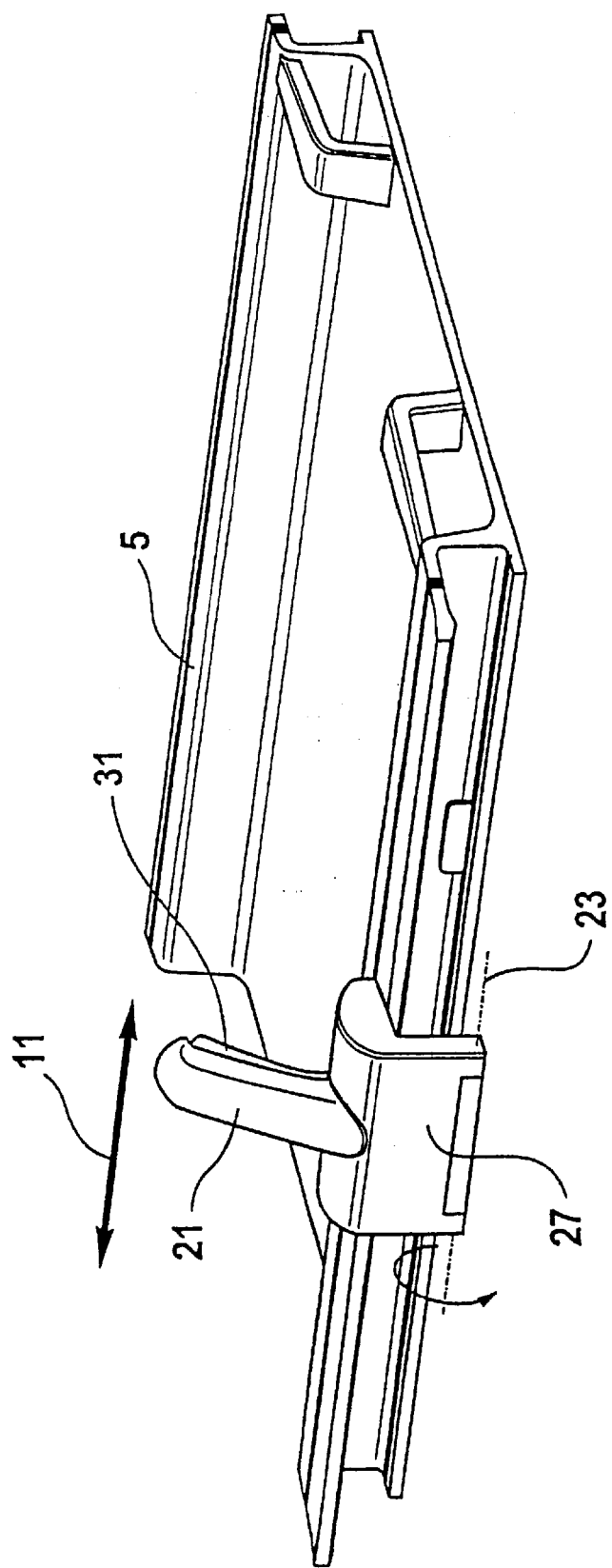
FIG. 3 shows the handle from FIG. 2 in a top position.

The panel 5 is shown in detail form in FIGS. 2 and 3. The handle 21 is arranged on the panel 5 such that it can be pivoted about a horizontal axis 23. In the top position of the handle 21, this position being illustrated in FIG. 3, said handle allows straightforward displacement of the panel 5.

A fastening part 25 is screwed, welded or riveted to the panel 5 and has a pivoting part 27 fitted on it in a pivotable manner. The fastening part 25 and the pivoting part 27 can be pivoted or tilted relative to one another by bearing pins 28. The fastening part 25 is a right-angled component with two legs, one of the legs butting horizontally, and one leg butting vertically, against the panel 5. The pivoting part 27 likewise has two legs 27-1, 27-2 which are located perpendicularly to one another and are adapted in size and shape to the corresponding legs of the fastening part 25, with the result that in the swung-together state, i.e. in the top position of the handle 21, the fastening part 25 and the pivoting part 27 terminate in a largely flush manner. In the example depicted, the pivoting part 27 also has, for this purpose, a recess or depression 29 for accommodating the fastening part 25.

The axis 23 runs through the end of that leg of the fastening part 25 which comes to rest vertically (geodetically)—in the top position of the handle 21 and through the end of the corresponding leg 27-2 of the pivoting part 27.

The handle 21 is fastened on the pivoting part 27, to be precise on the leg 27-2 directed away from the axis 23, on the side of the convex angle.

FIG. 3 shows the handle 21 in a first position, in which the handle is on the patient side or at the top. In this position, the pivoting part 27 has been swung up onto the shape-adapted fastening part 25 and latched in on the fastening part 25 by means of a snap-in closure 30.

Actuation of the snap-in closure 30 allows the pivoting part 27 to be released from the fastening part 25, with the result that it can be pivoted downward about the axis 23 into a second position, in which the handle is directed away from the patient 3 (FIG. 2). In this second position, it is not possible for the handle to obstruct any movement of the patient 3 onto, or away from, the patient-supporting apparatus.

Integrated in the handle 21 is a lever-like actuating element 31 which is connected to a nose 32 which passes through the relevant leg 27-2 of the pivoting part 27. The actuating element 31 and the nose 32 can be pivoted about the axis 23 together with the handle 21.

A braking device 33 is fitted in the panel 5 and has a contact element 35 projecting through the fastening part 25. When the contact element 35 is not actuated, the braking device 33 causes the panel 5 to be secured.

In the first position of the handle 21, this position being illustrated in FIG. 3, the nose 32 (which cannot be seen in FIG. 3) is positioned on the pivoting part 27 in relation to the contact element 35 such that actuation of the actuating element 31, and thus a movement of the nose 32, acts on the contact element 35, with the result that the braking action is eliminated or reduced.

What is claimed is:

1. A patient supporting apparatus for a piece of medical equipment, the apparatus comprising:
    a movable panel having an upper surface for supporting a patient or a further supporting panel;
    a guide element across which said panel is movable into an active region of a piece of medical equipment; and
    a pivotable handle for applying a force to said panel that moves said panel relative to said guide element, said handle being pivotable between a first position where said handle projects upward beyond said upper surface of said panel so that the force can be applied to said handle to move said panel into an active region of a piece of medical equipment and a second position where said handle is below said upper surface of said panel.

2. The apparatus of claim 1, wherein said handle is pivotable through a pivot angle of at least 150°.

3. The apparatus of claim 1, wherein said handle has a pivot axis that is parallel to said panel.

4. The apparatus of claim 1, further comprising a brake that prevents movement of said panel relative to said guide element.

5. The apparatus of claim 4, wherein said handle further comprises a brake actuator that is arranged to release said brake only when said handle is in the first position.

6. The apparatus of claim 5, wherein said brake actuator is a lever that is pivoted with said handle and that engages a contact element of said brake when said handle is in the first position.

7. The apparatus of claim 1, wherein said handle is a generally cylindrical member adapted to be gripped by a human hand.

8. The apparatus of claim 1, wherein said handle comprises a fastening part affixed to said panel and a pivoting part pivotally attached to said fastening part.

9. A patient supporting apparatus for a piece of medical equipment, the apparatus comprising:
    a movable panel having an upper surface for supporting a patient or a further supporting panel;
    a guide element below said panel and on which said panel is movable to move a patient to a piece of medical equipment;
    a fastening part affixed to said panel;

a pivoting part having a generally L-shape with a first leg having a distal end pivotally attached to said fastening part; and a handle attached to a second leg of said pivoting part, said pivoting part being pivotable between a first position where said second leg is directly adjacent to said fastening part and said handle projects upward above said panel and a second position where said second leg is spaced from said fastening part and said handle projects downward below said panel, said handle being arranged to receive a force that moves said panel relative to said guide element when said handle is the first position.

10. The apparatus of claim 9, further comprising a brake that prevents movement of said panel relative to said guide element, said brake having a contact that extends through said fastening part.

11. The apparatus of claim 10, further comprising a lever inside said handle that extends through said second leg and pivots with said pivoting part into engagement with said contact to release said brake, said lever engaging said contact only when said handle is in the first position.

12. The apparatus of claim 9, wherein said pivoting part is pivotable through a pivot angle of at least 150°.

13. The apparatus of claim 9, wherein said first claim wherein leg has a pivot axis that is parallel to said panel.

14. The apparatus of claim 9, wherein said handle is a generally cylindrical member adapted to be gripped by a human hand.

15. A patient supporting apparatus for a piece of medical equipment, the apparatus comprising:

a movable panel having an upper surface for supporting a patient or a further supporting panel;

a guide element below said panel and on which said panel is movable to move a patient to a piece of medical equipment;

a brake that prevents movement of said panel relative to said guide element;

a handle assembly having a fastening part affixed to said panel and a pivoting part with a first leg pivotally attached to said fastening part and a second leg with a handle, said pivoting part being pivotable between a first position where said second leg is mated with said fastening part and a second position where said second leg is spaced from said fastening part; and a brake actuator inside said handle and that pivots with said pivoting part into engagement with said brake to release said brake, said brake actuator releasing said brake only when said handle is in the first position.

16. The apparatus of claim 15, wherein said pivoting part is pivotable through a pivot angle of at least 150°.

17. The apparatus of claim 15, wherein said first leg has a pivot axis that is parallel to said panel.

18. The apparatus of claim 15, wherein said handle is a generally cylindrical member adapted to be gripped by a human hand.

* * * * *